United States Patent [19]

Lunn et al.

[11] 4,382,931

[45] May 10, 1983

[54] 3'-SUBSTITUTED QUINOLINIUM CEPHALOSPORINS

[75] Inventors: William H. W. Lunn; William J. Wheeler, both of Indianapolis, Ind.

[73] Assignee: Eli Lilly and Company, Indianapolis, Ind.

[21] Appl. No.: 300,141

[22] Filed: Sep. 8, 1981

[51] Int. Cl.$^3$ .................. A61K 31/545; C07D 501/46
[52] U.S. Cl. ..................................... 424/246; 544/22; 544/27; 544/28; 548/133; 548/233; 548/245
[58] Field of Search ..................... 424/246; 544/22, 27

[56] References Cited

U.S. PATENT DOCUMENTS 3,960,849  6/1976  Breuer ................................... 544/27
4,024,133  5/1977  Cook et al. ........................... 544/27
4,258,041  3/1981  O'Callaghan et al. ............. 424/246

OTHER PUBLICATIONS

Derwent Abstract No. 32890.

Primary Examiner—Paul M. Coughlan, Jr.
Attorney, Agent, or Firm—William B. Scanlon; Arthur R. Whale

[57] ABSTRACT

Broad spectrum cephalosporin antibiotics represented by the formula

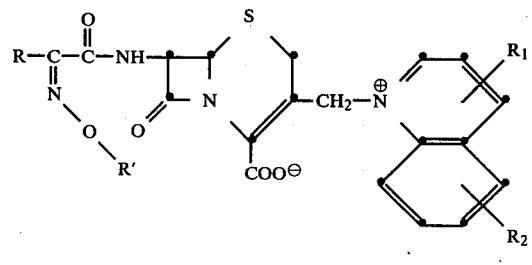

are provided. In the formula, R represents a 2-aminooxazol-4-yl, 5-amino-1,2,4-oxadiazol-3-yl, or 5-aminoisoxazol-3-yl heterocyclic group; R' is hydrogen, $C_1$–$C_4$ alkyl, a carboxy-substituted alkyl or cycloalkyl group or a $C_1$–$C_4$ alkyl ester or carboxy-protecting ester derivative thereof; or an N-substituted carbamoyl group; and $R_1$ and $R_2$ are independently hydrogen or a substituent group, eg. halo, hydroxy, amino, carbamoyl, alkyl, or trifluoromethyl. The antibiotics are useful in a method for treating bacterial infections and can be formulated into pharmaceutical formulations for such use.

13 Claims, No Drawings

3'-SUBSTITUTED QUINOLINIUM CEPHALOSPORINS

BACKGROUND OF THE INVENTION

This invention relates to semi-synthetic cephalosporin antibiotic compounds. In particular, it relates to cephalosporin compounds wherein the bicyclic cephalosporin nucleus is substituted in the 3'-position with quinolinium or a substituted quinolinium group, and in the 7-position with an acetamido group substituted by a 5-membered heterocyclic ring containing one or two nitrogen atoms and an oxygen atom, and an oxime group or substituted oxime group.

Cephalosporin compounds substituted in the 3'-position with a quaternary ammonium group have been known for some time. For example, cephalosporin $C_A$ (pyridine) was one of the first derivatives of cephalosporin C prepared by Abraham et al. following the discovery of cephalosporin C, Hale, Newton, and Abraham, *Biochem. J.*, 79, 403 (1961).

Cephaloridine, the well-known clinical antibiotic, is the 3'-pyridinium cephalosporin, 7-(α-thienylacetamido)-3-(pyridinium-1-ylmethyl)-3-cephem-4-carboxylate. Recently, Heymes et al., U.S. Pat. No. 4,152,432, described semi-synthetic cephalosporin antibiotics wherein the 7-position side chain is a 7-[2-(2-aminothiazol-4-yl)-2-alkoxyiminoacetamido] group and the 3'-position substituent is acetoxymethyl. More recently, O'Callaghan, et al., in U.S. Pat. No. 4,258,041, describe 7-[2-(2-aminothiazole-4-yl)-2-oximinoacetamido]-3-(pyridinium-1-ylmethyl)-3-cephem-4-carboxylate antibiotics, and the corresponding compounds wherein the pyridinium group in the 3'-position is substituted with a carbamoyl group. These cephalosporin compounds of Heymes and O'Callahan, et al., are reported to be highly effective antibacterial agents.

Because of the continuing need for improved antibiotic therapy in clinical practice, the search continues for broader spectrum antibiotics with greater potency and minimal toxicity. The semi-synthetic cephalosporin antibiotics long have been recognized as broad spectrum antibiotics, and several have achieved clinical importance. Continued research with the cephalosporin antibiotics has centered of late on the development of antibiotics having higher activity against certain gram-negative microorganisms such as pseudomonas and those which produce β-lactamase destructive of β-lactam antibiotics.

SUMMARY

This invention provides cephalosporin antibiotic compounds represented by the formula

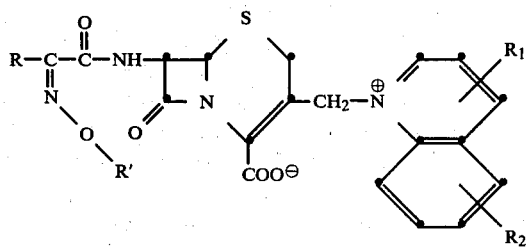

wherein R is a 5-membered amino-substituted oxygen containing heterocyclic ring, eg. 2-aminooxazole, R' is hydrogen, a lower alkyl group, an N-substituted carbamoyl group, a carboxy-substituted alkyl or cycloalkyl group or the primary amides thereof, and $R_1$ and $R_2$ represent hydrogen or a substituent group.

The compounds are prepared by displacement of an acetoxy or halo group in the 3'-position of a cephalosporin having the same 7-position side chain as described above, with quinoline or the substituted quinoline. Preferably, the compounds described herein are prepared with the 3-iodomethyl substituted cephalosporins.

The compounds of the invention are highly active antibacterial agents useful in combatting the growth of microorganisms pathogenic to man and animals. Pharmaceutical formulations comprising a compound of the invention are provided as well as a method for treating bacterial infections.

DETAILED DESCRIPTION

The cephalosporin compounds of the invention are represented by the following formula 1

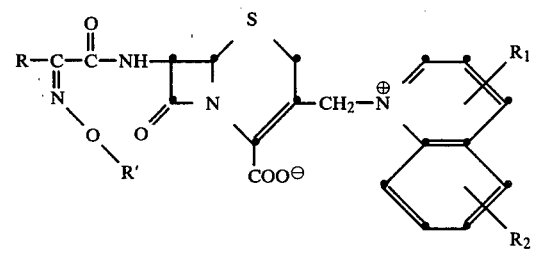

wherein R is an amino-substituted heterocyclic of the formulas

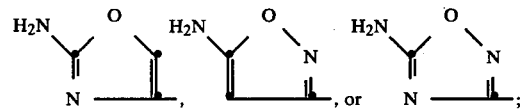

R' is hydrogen, $C_1$–$C_4$ alkyl, a carboxy-substituted alkyl or carboxy-substituted cycloalkyl group represented by the formula

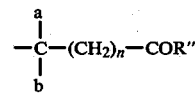

wherein n is 0–3; a and b when taken separately are independently hydrogen or $C_1$–$C_3$ alkyl, and when taken together with the carbon atoms to which they are attached form a $C_3$–$C_7$ carbocyclic ring, and wherein R" is hydroxy, amino or $C_1$–$C_4$ alkoxy, and, when R" is hydroxy, the carboxy-protected esters thereof; or R' is an N-substituted carbamoyl group represented by the formula

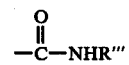

wherein R''' is $C_1$–$C_3$ alkyl, phenyl, or $C_1$–$C_3$ alkyl substituted by phenyl; $R_1$ and $R_2$ independently are hydrogen, amino, $C_1$–$C_4$ alkylamino, di-($C_1$–$C_4$)alkylamino, hydroxy, $C_1$–$C_4$-alkoxy, halogen, $C_1$–$C_4$ alkyl, cyano, trifluoromethyl, sulfo(—$SO_3H$), aminosulfonyl (—SO$_2$NH$_2$), carboxy, C$_1$–C$_4$ alkoxycarbonyl, carbamoyl, thiocarbamoyl, hydroxy-substituted C$_1$–C$_3$ alkyl, formyl, or C$_2$–C$_4$ alkanoyl; and the pharmaceutically acceptable non-toxic salts thereof.

In the above formula 1 the term C$_1$–C$_4$ alkyl refers to methyl, ethyl, n-propyl, iso-propyl, n-butyl, sec-butyl, and like lower alkyl radicals; C$_1$–C$_3$ alkyl substituted by phenyl refers to benzyl, 2-phenethyl, 3-phenylpropyl, 2-phenylpropyl and the like; C$_1$–C$_4$ alkylamino refers to methylamino, ethylamino, n-propylamino, n-butylamino, iso-propylamino, and like mono lower alkyl amino groups; di(C$_1$–C$_4$ alkyl) amino refers to dimethylamino, diethylamino, methylethylamino, di(n-butyl)amino, di-(n-propyl)amino, and the like; C$_1$–C$_4$ alkoxy refers to methoxy, ethoxy, n-propoxy, iso-propoxy, n-butoxy, t-butoxy, and the like; C$_1$–C$_4$ alkoxycarbonyl refers to methoxycarbonyl, ethoxycarbonyl, isopropoxycarbonyl, t-butoxycarbonyl, and the like; and examples of C$_2$–C$_4$ alkanoyl groups include acetyl, propionyl, butyryl, and the like.

Examples of carbamoyl groups represented by R' in the formula 1 are N-methylcarbamoyl, N-ethylcarbamoyl, N-phenylcarbamoyl, N-benzylcarbamoyl, N-(1-phenylethyl)carbamoyl and N-(2-phenylethyl)carbamoyl.

Examples of carboxy-substituted alkyl and cycloalkyl groups represented by R' in formula 1 wherein R" is hydroxy are carboxymethyl, 2-carboxyethyl, 3-carboxypropyl, 2-carboxyprop-2-yl, 2-carboxy prop-1-yl, 1-carboxyethyl, 1-carboxycycloprop-1-yl, 1-carboxycyclobut-1-yl, 1-carboxycyclopent-1-yl, 1-carboxycyclohex-1-yl, 1-carboxymethylcyclobut-1-yl, 1-(3-carboxypropyl)cyclopent-1-yl, and the like; and when R" is amino, examples of such carboxamido-substituted alkyl and cycloalkyl groups are the primary amides of the carboxy-substituted alkyl and carboxy-substituted cycloalkyl groups named above.

When R" in the formula 1 is hydroxy, the carboxy group represented can be protected by a carboxy-protecting ester group. Such carboxy-protecting ester groups include those readily removable ester groups commonly used in the β-lactam art for the temporary protection of the carboxy group. Examples of such groups are t-butyl, 2,2,2-trichloroethyl, 2-iodomethyl, benzyl, diphenylmethyl, p-nitrobenzyl, p-methoxybenzyl, and trialkylsilyl groups such as trimethylsilyl, and like groups.

The substituted quinolinium group in the 3'-position of the compounds of the invention (formula 1) is exemplified by the following: amino-substituted quinolinium groups such as 3-aminoquinolinium, 4-aminoquinolinium, 5-aminoquinolinium, 3,6-diaminoquinolinium, 4-amino-8-methylquinolinium, 3-methoxy-5-aminoquinolinium, 3-amino-7-cyanoquinolinium, 4-amino-6-acetylquinolinium, 5-amino-8-sulfoquinolinium, 4-amino-5-trifluoromethylquinolinium, 3-chloro-5-aminoquinolinium, and the like; C$_1$–C$_4$ alkyl and di-(C$_1$–C$_4$alkyl)amino-substituted quinolinium groups such as 3-methylaminoquinolinium, 3-dimethylaminoquinolinium, 5-diethylaminoquinolinium, 3-ethyl-5-ethylaminoquinolinium, 3-ethyl-5-di(n-propyl)aminoquinolinium, 6-chloro-3-n-butylaminoquinolinium, 6-bromo-4-dimethylaminoquinolinium, and the like; hydroxy-substituted quinolinium groups such as 3-hydroxyquinolinium, 5-hydroxyquinolinium, 3-hydroxy-5-cyanoquinolinium, 5-hydroxy-6-aminoquinolinium, 3-methyl-5-hydroxyquinolinium, 4-carbamoyl-8-hydroxyquinolinium, and the like; C$_1$–C$_4$ alkoxy-substituted quinolinium groups such as 3-methoxyquinolinium, 8-ethoxyquinolinium, 7-isopropoxyquinolinium, 3-chloro-5-methoxyquinolinium, and the like; haloquinolinium groups such as 4-chloroquinolinium, 3-methyl-4-chloroquinolinium, 5-bromoquinolinium, 3,7-dichloroquinolinium, 3-hydroxy-5-chloroquinolinium, 3-cyano-5-bromoquinolinium, 4-carbamoyl-5-chloroquinolinium, and the like; cyanoquinolinium groups such as 3-cyanoquinolinium, 3-ethyl-6-cyanoquinolinium, 4-chloro-6-cyanoquinolinium, 5-cyanoquinolinium, 3-chloro-5-cyanoquinolinium, 3-amino-5-cyanoquinolinium, and the like; trifluoromethyl and alkyl-substituted quinolinium groups such as 3-trifluoromethylquinolinium, 5-trifluoromethylquinolinium, 8-trifluoromethylquinolinium, 3-methyl-4-trifluoromethylquinolinium, 4-chloro-6-trifluoromethylquinolinium, 4-cyano-6-trifluoromethylquinolinium, 3-carboxy-5-trifluoromethylquinolinium, 4-t-butylquinolinium, 3-methylquinolinium, 6-n-propylquinolinium, and the like; formyl and C$_2$–C$_4$ alkanoyl substituted quinolinium groups such as 3-formylquinolinium, 3-acetylquinolinium, 4-formylquinolinium, 4-formyl-6-chloroquinolinium, 3-methoxy-6-acetylquinolinium, 5-butyrylquinolinium, 8-cyano-5-acetylquinolinium, and the like; carbamoyl and thiocarbamoyl-substituted quinolinium groups such as 4-carbamoylquinolinium, 4-thiocarbamoylquinolinium, 5-carbamoylquinolinium, 3-carbamoyl-5-hydroxyquinolinium, 8-chloro-4-carbamoylquinolinium, 3-trifluoromethyl-5-carbamoylquinolinium, 3-methyl-5-thiocarbamoylquinolinium, 6-carbamoyl-3-ethylquinolinium, and the like; and sulfo, sulfonamido, hydroxy-C$_1$–C$_3$ alkyl, and carboxy-substituted quinolinium groups such as 5-sulfoquinolinium, 4-sulfoquinolinium, 3-hydroxymethylquinolinium, 4-sulfonamidoquinolinium, 3-methyl-5-sulfoquinolinium, 4-carboxyquinolinium, 6-carboxyquinolinium, 4-chloro-6-carboxyquinolinium, 3-acetyl-5-carboxyquinolinium, 6-fluoro-3-sulfonamidoquinolinium, 6-(2-hydroxyethyl)-3-methylquinolinium, and like mono- and di-substituted quinolinium groups.

The amino-substituted heterocyclic ring groups represented by R in formula 1 are named herein as the 2-aminooxazol-4-yl, 5-aminoisoxazol-3-yl, and the 5-amino-1,2,4-oxadiazol-3-yl group.

The compounds of the formula 1 can be prepared by alternative methods. According to a preferred method for preparing the compounds, a 7-acylamino-3-acetoxymethyl cephalosporin, wherein the 7-acyl group is as defined for the formula 1, is converted to a 3-halomethyl derivative, and the 3-halomethyl derivative is reacted with quinoline or a substituted quinoline to obtain a compound of the invention. The method of preparation is illustrated by the following reaction scheme.

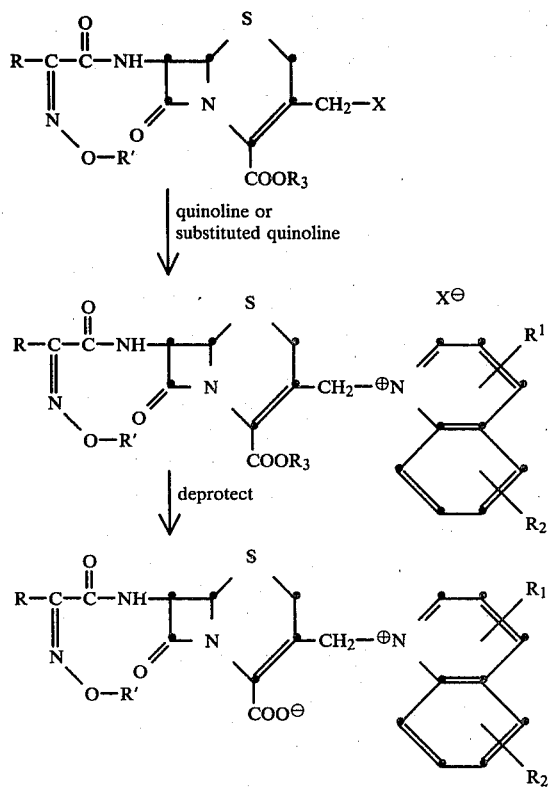

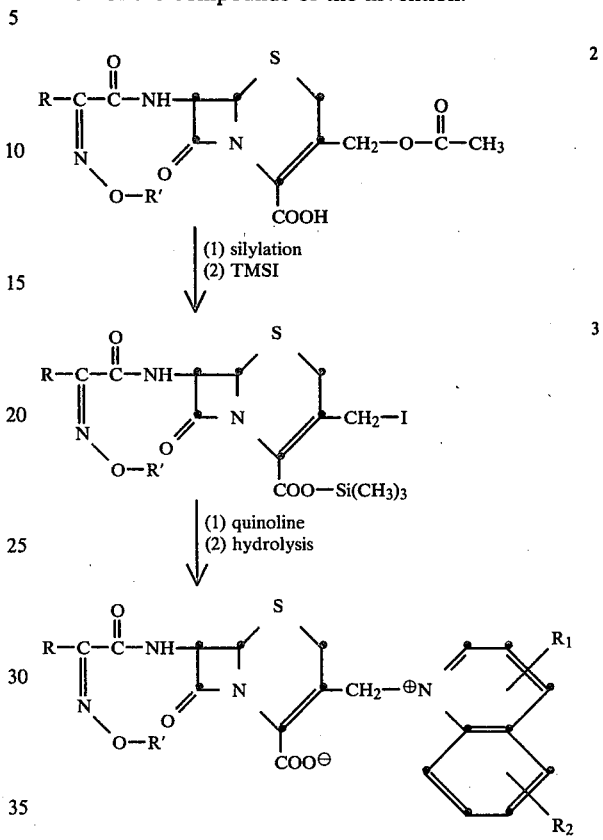

In the above formulas, R, R', $R^1$ and $R^2$ have the same meanings as defined hereinabove, X is chloro, bromo, or iodo, and $R_3$ is a carboxy-protecting group. The carboxy-protecting group, $R_3$, can be a readily removable ester group, such as is described hereinabove for the term R''. Preferably, $R_3$ is a trialkylsilyl group eg., trimethylsilyl.

The preferred method for preparing the compounds of the invention comprises the use of a 7-acylamino-3-iodomethyl derivative wherein the carboxy and amino groups are protected by silylation such as with a lower trialkylsilyl group, preferably trimethylsilyl. In carrying out the preparation of a compound of the invention by the preferred method, the 7-acylamino-3-acetoxymethyl-3-cephem-4-carboxylic acid is first silylated to block the reactive carboxyl and amino functional groups present in the molecule. The silylation is carried out with one of the commonly employed silylating agents, for example, mono- or bis-trimethylsilylacetamide or, preferably, with N-methyl-N-trimethylsilyltrifluoroacetamide. The silylation is carried out in an inert solvent such as a halogenated hydrocarbon solvent, for example, methylene chloride, chloroform, chloroethane, or other inert organic solvent such as acetonitrile or propionitrile. The silylated derivative is then allowed to react with trimethylsilyliodide (TMSI) to form the corresponding 3-iodomethyl silylated derivative. The reaction mixture containing the silylated 3-iodomethyl derivative is evaporated to remove the solvent, and the concentrate is dissolved in acetonitrile and is treated with a slight excess of tetrahydrofuran to degrade any excess TMSI. To this solution is then added quinoline or the substituted quinoline to form a compound of formula 1 as the silylated derivative. Upon the addition of water, the silyl derivative is hydrolyzed to form a compound of the invention.

The following reaction scheme illustrates the preparation of the compounds of the invention.

The preparation of the 3-iodomethylcephalosporin intermediate is carried out according to the process described by Bonjouklian in U.S. Pat. No. 4,266,049, issued May 8, 1981. In carrying out the preparation of the 3-iodomethylcephalosporin, other trialkylsilyl iodides may be employed as described by Bonjouklian. Trimethylsilyl iodide is the preferred reagent and is used to illustrate the preparation of the compounds herein.

In an example of the preparation of a compound of the invention, syn-7-[2-(2-aminooxazol-4-yl)-2-methoxyiminoacetamido]-3-acetoxymethyl-3-cephem-4-carboxylic acid is suspended in an inert organic solvent such as chloroform and is silylated by employing N-methyl-N-trimethylsilyltrifluoroacetamide. A complete solution is obtained upon silylation. To the solution is then added trimethylsilyl iodide in at least a stoichiometric amount and, preferably, 2 to 3 times the stoichiometric amount. The mixture is stirred to assure complete formation of the 3-iodomethyl derivative. The 3-iodomethyl derivative need not be isloated and, preferably, is used as the silylated derivative in the next step of the reaction. Accordingly, the reaction mixture containing the silylated 3-iodomethyl derivative is evaporated to remove volatiles, for example, solvent, and is then dissolved in acetonitrile. To the solution is added tetrahydrofuran and the solution is stirred for a short while. The treatment of the silylated 3-iodomethyl derivative solution with tetrahydrofuran degrades any excess TMSI. The degradation of the complex enhances the recovery and purity of the final product.

The solution of the silylated 3-iodomethyl derivative is then mixed with a solution of quinoline in a suitable solvent such as acetonitrile. The reaction occurs readily and most conveniently at room temperature with stirring. After the reaction is complete, water is added to the mixture to hydrolyze the silyl-blocking groups, for example, the silyl ester formed with the C4 carboxylic acid function. Following the addition of the water to the reaction mixture, the product commonly precipitates and is separated by filtration, centrifugation, or other suitable means. The product is generally crude at this stage of its preparation and can be purified by high performance liquid chromatography on reversed-phase $C_{18}$ silica gel using a solvent system of acetonitrile/acetic acid/water containing approximately 2% acetic acid and between about 10% and about 20% of acetonitrile.

The compounds of the invention can be prepared alternatively by acylation of a 7-amino-3-(quinolinium or substituted quinolinium-1-ylmethyl)-3-cephem-4-carboxylate. The 3'-quaternary ammonium substituted nucleus compounds are prepared by reacting 7-aminocephalosporanic acid or a silylated derivative thereof with the quinoline. The substituted nucleus is then acylated with an oximino-substituted derivative of the desired amino-substituted heterocyclic acetic acid represented by the formula

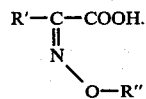

An active derivative of the oximino acetic acid is used in the acylation. For example, the acid group is reacted with hydroxybenzotriazole (HBT) and a carbodiimide such as dicyclohexylcarbodiimide, and the HBT ester which is formed is used to acylate the 7-amino group of the nucleus. Other active derivatives such as the acid azide, the anhydride formed with methyl chloroformate or isobutyl chloroformate, can be used for acylation.

The 3'-quaternary nucleus compounds also can be prepared by the N-deacylation of a 7-acylamino-3-(quinolinium or substituted quinolinium-1-ylmethyl)-3-cephem-4-carboxylate wherein the 7-acyl group is other than R' (formula 1). The 7-acyl group can be, for example, phenoxyacetyl, phenylacetyl, or 2-thienylacetyl. The deacylation is carried out by the well known procedure for the 7-position side chain deacylation of cephalosporins and desacetoxycephalosporins in the preparation of 7-aminocephalosporanic acid and 7-aminodesacetoxycephalosporanic acid. According to the method, a 7-acylaminocephalosporin is reacted with an imino halide-forming reagent, such as phosphorus pentachloride or phosphorus trichloride, to form the imino chloride of the 7-amido bond. The imino chloride is converted to the imino ether with an alcohol and the imino ether is hydrolyzed to the 7-amino nucleus compound.

In an example of the preparation of a 7-amino-3-(quinolinium or substituted quinolinium-1-ylmethyl)-3-cephem-4-carboxylate, 7-(α-thienylacetamido)cephalosporanic acid is reacted with quinoline to form the 7-(α-thienylacetamido)-3-(quinolinium-1-yl-methyl)-3-cephem-4-carboxylate. The latter is then reacted in an inert halogenated hydrocarbon solvent such as methylene chloride or trichloroethane at a temperature between about −20° C. and about 25° C. with phosphorus pentachloride in the presence of an organic base such as pyridine or N,N-dimethylaniline. After imino chloride formation is complete, an alcohol such as a $C_1$–$C_4$ alkanol, benzyl alcohol, or a glycol such as propylene glycol is added to the reaction mixture at about −20° C. to about 5° C. After imino ether formation is complete, the reaction mixture is allowed to warm to ambient temperature and the product precipitates as the dihydrochloride salt.

During the N-deacylation, any reactive substituent groups of the substituted quinolinium group ($R_1$ and $R_2$) are protected from reaction with the imino halide-forming reagent. For example, an amino group or carboxy substituent is protected. Since the 7-amino nucleus compound is used in the preparation of compounds of the invention via the above-described acylation, the protected substituent group is preferably left intact to likewise protect the substituent group during the subsequent N-acylation.

The compounds of the invention can be prepared by another alternative procedure comprising the displacement of the acetoxy group of the desired 7-acylamino-3-acetoxymethyl cephalosporin with the quinoline. The reaction is illustrated as follows.

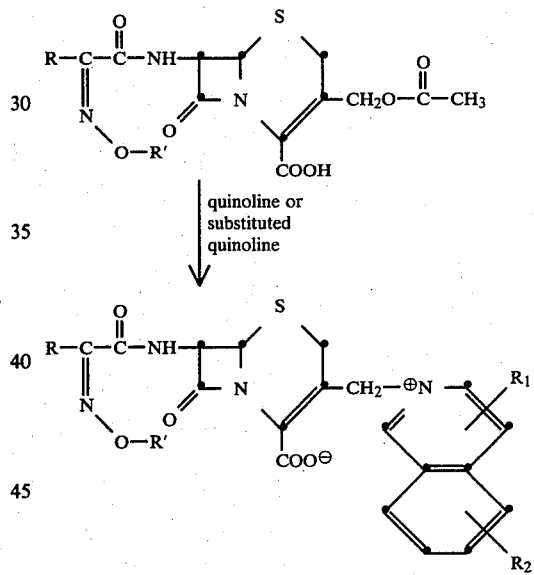

The reaction is carried out in an aqueous solvent system of water and a water miscible organic solvent such as acetone, DMF, DMAC or other suitable solvent at a temperature between about 20° C. and about 55° C. A small amount of an alkali metal iodide such as sodium iodide may be added to the reaction mixture to enhance the reaction rate and yield of the reaction.

The 7-[2-(aminoheterocyclic)-2-oximino- and 2-substituted oximinoacetamido]-3-acetoxymethyl-3-cephem-4-carboxylic acids, represented by the above formula 2, which are used to prepare the compounds of the invention can be prepared by known methods as described herein.

The 7-[2-(amino-substituted oxazole and oxadiazole)-2-oximinoacetamido]-3-acetoxymethyl-3-cephem-4-carboxylic acids represented by the formula 2 are prepared by the methods described by Wheeler in copending applications Ser. Nos. 300,140 and 300,159, filed this even date. As described therein, the 7-[2-(2-aminooxazol-4-yl)-2-methoximinoacetamido]-3-acetoxymethyl-3-cephem-4-carboxylic acid and the corresponding 5-amino-1,2,4-oxadiazol-3-yl compound are prepared by the acylation of an ester of 7-aminocephalosporanic acid with the 2-(2-aminooxazol-4-yl)-2-methoximinoacetic acid and the 2-(5-amino-1,2,4-oxadiazol-3-yl)-2-methoximinoacetic acid, respectively.

The 2-(5-amino-1,2,4-oxadiazol-3-yl)-2-methoximinoacetic acid is prepared by reacting an ethyl 2-oximinocyano acetate represented by the formula

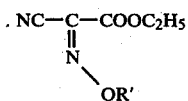

wherein R' is other than hydrogen, with hydroxylamine to obtain a 2-ethoxycarbonyl-2-oximinoacetoxime amide represented by the formula

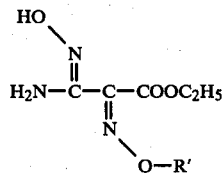

The latter intermediate is reacted with trichloroacetyl chloride to form the cyclization product, an ethyl 2-(5-trichloromethyl-1,2,4-oxadiazol-3-yl)-2-oximinoacetate, represented by the formula

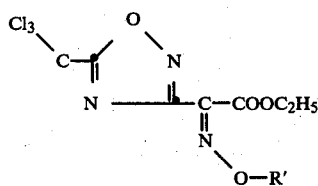

Upon reaction with ammonia the trichloromethyl substituent is replaced with the amino group to provide the 5-aminooxadiazole derivative represented by the formula

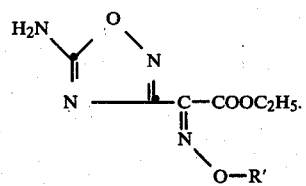

The oximino group of the trichloromethyl substituted oxadiazole is in both the syn and anti forms. During the aminolysis reaction the anti (E) compound forms the amide, 2-(5-amino-1,2,4-oxadiazol-3-yl)-2-oximinoacetamide, while the syn (Z) compound does not. Owing to its lower solubility the anti-amide is readily separated from the syn ester. The syn ethyl 2-(5-amino-1,2,4-oxadiazol-3-yl)-2-oximinoacetate is saponified in aqueous ethanolic sodium hydroxide to sodium syn-2-(5-amino-1,2,4-oxadiazol-3-yl)-2-oximinoacetate and the free acid obtained with the salt by treating the salt with hydrochloric acid.

The preparation of the 2-(5-amino-1,2,4-oxadiazol-3-yl)-2-oximinoacetic acid wherein R' is hydrogen is carried out as described above with the oxime protected by a hydroxy-protecting group such as the chloroacetyl group. During the saponification of the ethyl ester the protecting group is also removed. When R' is a carboxy-substituted alkyl or cycloalkyl group, the 2-oximinocyano acetate represented by the formula,

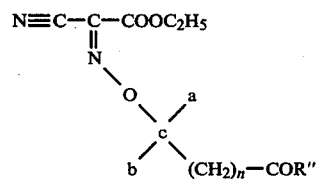

wherein R" is amino or $C_1-C_4$ alkoxy is used in the above-described synthesis. When R" is hydroxy, the carboxy group thus represented is protected with a carboxy-protecting group, preferably one that is acid labile such as the p-methoxybenzyl or diphenylmethyl ester group. When R' is an N-substituted carbamoyl group, the heterocyclic free acid wherein R' is hydrogen is acylated with the desired carbamoyl chloride. The carboxy group of the 2-(2-amino-1,2,4-oxadiazol-3-yl)-2-oximinoacetic acid wherein R' is hydrogen is protected with an acid labile ester protecting group, and the oxime group is acylated with the desired carbamoyl chloride, e.g., N-methylcarbamoyl chloride, to provide the desired oximino derivative.

The 2-(2-aminooxazol-4-yl)-2-methoximinoacetic acid is prepared by the zinc oxide catalyzed condensation of urea, a γ-bromo-α-methoximinoacetoacetic ester in a suitable organic solvent. Convenient esters are the methyl and ethyl esters. Suitable solvents are the ketones such as acetone, methylethylketone, diethylketone, or methylisobutylketone. The condensation is carried out by suspending zinc oxide in a solution of the urea and the bromoacetoacetic ester in the ketone solvent, and heating the suspension for about 60 hours to about 120 hours. The product is isolated by evaporating the reaction mixture and extracting the product from the concentrate with ethyl acetate. The product is purified by chromatography over alumina.

The 2-(2-aminooxazol-4-yl)-2-methoxyiminoacetic acid is prepared by the saponification of the above ester wherein the 2-amino group is protected. For example, ethyl 2-(2-aminooxazol-4-yl)-2-methoxyiminoacetate is reacted in dimethylacetamide with chloroacetyl chloride in the presence of an acid-binding agent such as a tertiary amine, e.g., triethylamine, to form the amino-protected derivative, 2-[2-(2-chloroacetamido)oxazol-4-yl]-2-methoxyiminoacetate. The latter is then deesterified with aqueous sodium hydroxide to sodium 2-(2-aminooxazol-4-yl)-2-methoxyiminoacetate. Upon acidification, the free acid is obtained. During the saponification the amino-protecting chloroacetyl group is likewise removed.

The above-described preparation of the 2-aminooxazole oximino acid is illustrated by the following reaction scheme.

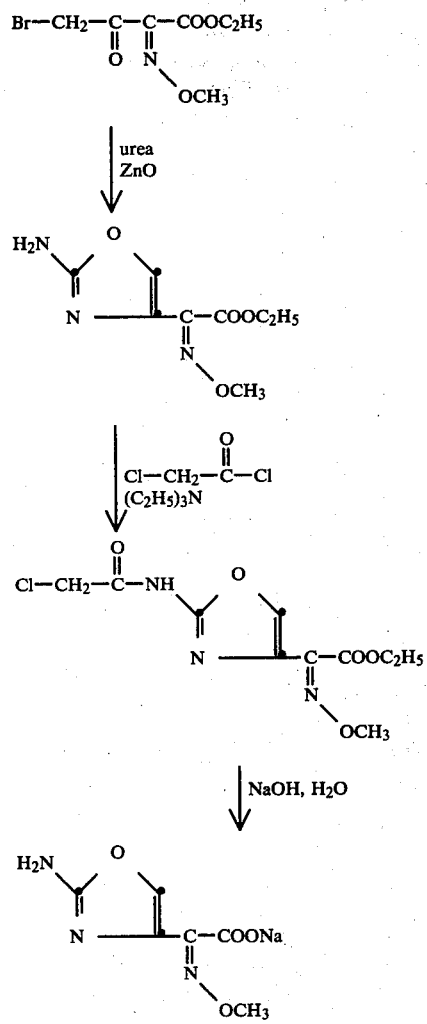

The compounds of the formula 2 are prepared by acylating 7-aminocephalosporanic acid as illustrated by the following reaction scheme.

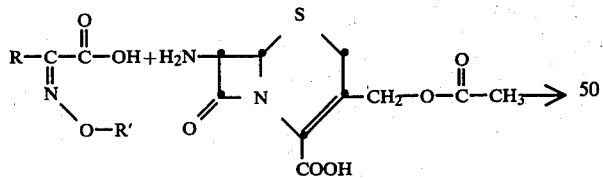

formula 2

The acylation is preferably carried out with an active derivative of the oximino-substituted acid, for example with an acid halide, acid azide, or an ester. Active esters formed with ethyl chloroformate or isobutyl chloroformate, or with hydroxybenzotriazole (HBT) are suitable in the acylation. The acylation can be carried out in an aqueous or a non-aqueous medium. In a non-aqueous medium an ester of 7-ACA is used in a solvent such as a halogenated hydrocarbon eg., methylene chloride or chloroform, or other suitable solvent such as acetonitrile or tetrahydrofuran. Alternatively, a suspension of 7-ACA in a suitable aprotic solvent can be converted to a soluble silyl ester such as a trialkylsilyl ester and the ester acylated under non-aqueous conditions.

Aqueous acylations can be carried out in water-miscible organic solvents containing water, eg., acetone-water, tetrahydrofuran-water and the like. For example, an acid halide of the acid moiety can be used to acylate 7-ACA in the presence of a base such as sodium carbonate, sodium bicarbonate, or a tertiary amine such as triethylamine or pyridine.

The compounds of the invention represented by the formula 1 have the normal stereochemistry of the known cephalosporin antibiotics. The 7-position side chain has the β-configuration (6R, 7R). The oximino group of the side chain can be in either the syn or anti form or as a mixture of both forms. Both the syn and anti forms of the compounds and the salts thereof possess broad spectrum antibacterial activity; however, the syn-form exhibits greater activity than the anti form and is the preferred form of the compounds of the invention. The compounds of the invention are obtained in the syn form by carrying out the acylation of 7-ACA or the 3'-substituted quinolinium nucleus with the syn form of the 2-(aminoheterocyclic)-2-oximinoacetic acid acylating moiety. For purposes of the acylation, the amino group of the heterocyclic ring in the 7-position side chain may be protected as described hereinabove.

The compounds of the invention form acid addition salts. Also, the compounds of the invention wherein R' is a carboxy-substituted alkyl or carboxy-substituted cycloalkyl group (R" is hydroxy) form salts of the carboxylic acid group. Such salts as the alkali metal salts, for example, the sodium salt, potassium salt, and the like, are useful pharmaceutically acceptable salts which can be used in formulating the antibiotics for use in treating infections. Salts formed with strong acids such as hydrochloric acid, hydrobromic acid, sulfuric acid, or phosphoric acid can be represented by the partial formula

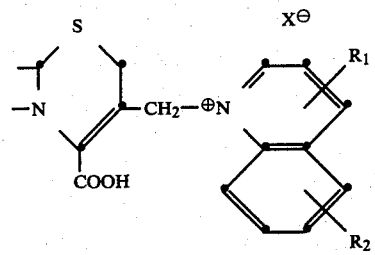

wherein $X^{\ominus}$ is the anion formed from the strong acid, e.g., chloride from hydrochloric acid.

Such acid addition salts are also useful pharmaceutically acceptable antibiotic salts. It will be appreciated that an amino or carboxy substituent group of the substituted quinolinium group in the 3'-position also can be converted to the salt form.

Preferred compounds of the invention are represented by the formula 1 wherein R is 2-aminooxazol-4-yl or 5-amino-1,2,4-oxadiazol-3-yl, R' is methyl and $R_1$ and $R_2$ are both hydrogen. Another preferred group is represented by formula 1 wherein R is 2-aminooxazol-4-yl or 5-amino-1,2,4-oxadiazol-3-yl, R' is methyl, and either of $R_1$ and $R_2$ is amino, hydroxy or carbamoyl, and the other is hydrogen.

The compounds of the formula 1 and the pharmaceutically acceptable non-toxic salts thereof possess valuable broad spectrum antibacterial properties. These compounnds are effective in inhibiting the growth of gram negative microorganisms pathogenic to man and animals such as pseudomonas, hemophilus, proteus, enterobacter, shigella, salmonella and other genera. They also inhibit the growth of the gram positive microorganisms such as the staphylococci, including methicillin-resistant staphylococci, and streptococci.

The antibiotic compounds represented by the formula 1 and the pharmaceutically acceptable non-toxic salts thereof can be formulated into pharmaceutical compositions suitable for use in the treatment of infectious diseases in man and animals. According to a further aspect of this invention, there are provided antibiotic formulations comprising an antibiotic compound of the formula 1 and a pharmaceutically acceptable carrier. Formulations for parenteral administration made up prior to use comprise the antibiotic or a salt thereof at a suitable concentration in a diluent such as Water-For-Injection, 5% dextrose, 0.9% saline, Ringer's solution, or other physiologically compatible diluent. The concentration in the diluent can vary depending upon the mode of parenteral administration. For intramuscular administration the concentration of the antibiotic in general can be between about 0.1 g./ml. to about 1 g./ml. For intravenous administration the antibiotic or a salt thereof is formulated in a physiological fluid, such as one of those described above, and the formulation administered by the i.v. drip method.

The antibiotics also can be formulated in dosage unit form comprising between about 100 mg. and 2 g. of the dry antibiotic in solid form in sterile capped vials or sterile hermetically sealed ampoules. In such forms the antibiotic may be in amorphous or crystalline form and may be mixed with a buffer, desiccant, or blending agent. Such dosage unit formulations are suitable for storage and shipment of the antibiotic and, as with other antibiotics, upon dissolution in the desired diluent in the vial or ampoule the solution is withdrawn by syringe and injected.

This invention also provides a method for treating bacterial infections in mammals which comprises administering in a dose of between about 100 mg. to about 2.0 g. of body weight of a compound of the formula 1 or a pharmaceutically acceptable non-toxic salt thereof.

The antibiotic may be administered intramuscularly, subcutaneously, or intravenously in a single dose or in multiple doses during the day. When administered i.v. the infusion method is conveniently employed. For example, a dosage unit formulation of the antibiotic is mixed with a physiological fluid such as 5% dextrose and administered by infusion.

In practicing the method of this invention, the particular dosage and the total number of doses administered will depend on such factors as the nature of the infection, its severity, the age and general health of the patient, as well as the tolerance of the individual to the antibiotic.

The following Preparations and Examples further illustrate the invention. The abbreviations used in the Preparations and Examples have the following meanings: HPLC is high performance liquid chromatography; E refers to the anti form of the oxime; Z refers to the syn form of the oxime; DMSO/$d_6$ is deuterated dimethylsulfoxide; acetone/$d_6$ is deuterated acetone; n.m.r is nuclear magnetic resonance spectrum; the letters used to characterize the signals in the n.m.r. spectra refer to the following: s is singlet; d is doublet; q is quartet; m is multiple; J is the coupling constant in Hertz; br s is broad singlet; and t is triplet.

PREPARATION 1

Preparation of 2-[(5-Amino-1,2,4-oxadiazol)-3-yl]-2-methoxyimino acetic acid

Step A

Preparation of 2-Ethoxycarbonyl-2-methoximinoacetoxime amide

Ethyl 2-methoxyiminocyanoacetate (8 g., 51.2 mmol) was dissolved in ethanol (2B, 20 ml.) and the solution was added dropwise to a mixture of hydroxylamine hydrochloride salt (3.56 g., 51.2 mmol) and sodium carbonate (2.72 g., 25.6 mmol) in 3:2 v:v ethanol/water mixture (25 ml.). After the addition was complete the mixture was stirred and heated at the reflux temperature for approximately sixteen hours. The ethanol was then removed in vacuo and the remaining mixture was further diluted with water and then extracted with ethyl acetate. The ethyl acetate layer was washed with water (3X), dried over magnesium sulfate, filtered and concentrated to an oil in vacuo. The resultant oil later crystallized and was recrystallized from ethanol (2B) to yield 750 mg. of the product, 2-ethoxycarbonyl-2-methoximinoacetoxime amide: n.m.r. ($d_6$-DMSO) δ0.82 (t, 3, C$\underline{H}_3$CH$_2$), 3.5 (s, 3, OC$\underline{H}_3$), 3.62 (q, 2, CH$_3$C$\underline{H}_2$—), 5.0 (br s, 2, —N$\underline{H}_2$), 10.15 (s, 1, =NO$\underline{H}$).

Step B

Preparation of Ethyl 2-[(5-Trichloromethyl-1,2,4-oxadiazol)-3-yl]-2-methoxyimino Acetate 2-Ethoxycarbonyl-2-methoximinoacetoxime amide (7.65 g., 40 mmol) and pyridine (5 ml., 45 mmol) were dissolved in dioxane (25 ml.) and the solution cooled to 10° C. While stirring this solution, trichloroacetyl chloride (5 ml., 45 mmol) was added dropwise. The mixture was then allowed to warm to room temperature and the stirring was continued for approximately sixteen hours. The mixture was filtered to remove the pyridine hydrochloride and the filtrate was evaporated to dryness.

The residue was triturated with ether and decanted. The ether layer was washed with a saturated aqueous solution of sodium bicarbonate (2X) and then with water (2X), dried over magnesium sulfate, filtered and concentrated. The solid mass remaining was triturated with hexane and decanted. The remaining solid, which was unreacted starting material, was recrystallized from methanol. The hexane solution from the above decantation was evaporated to yield the product compound, ethyl 2-[(5-trichloromethyl-1,2,4-oxadiazol)-3-yl]-2-methoxyimino acetate:(isomeric mixture) mass spectrum:M+ 315.

Step C

Preparation of Ethyl 2-[(5-Amino-1,2,4-oxadiazol)-3-yl]-2-Z-methoximinoacetate

Ethyl 2-[(5-trichloromethyl-1,2,4-oxadiazol)-3-yl]-2-methoximinoacetate (7.62 g.) was dissolved in ether (40 ml.) and the solution added dropwise to anhydrous ammonia (250 ml.) with stirring. Stirring was continued while the ammonia evaporated overnight. The residue was triturated thoroughly with ether. Filtration yielded 1.1 g. of the undesired 2-[(5-amino-1,2,4-oxadiazol)-3- yl]-2-E-methoximinoacetamide. The filtrate from above was concentrated in vacuo then recrystallized from 2B ethanol to give 2.2 g. of the crude title product.

The crude product was combined with ethyl 2-[(5-amino-1,2,4-oxadiazol)-3-yl]-2-Z-methoximinoacetate (0.83 g.) made in a previous experiment analogous to the instant procedure. This mixture was dissolved partially in methylene chloride and filtered. The filtrate was chilled to −40° overnight then filtered again. The filtrate was evaporated to dryness and the residue was crystallized from 2B ethanol, yielding 0.209 g. of crystals of the title product. The mother liquor of this crystallization was concentrated and the residue was also recrystallized from 2B ethanol, yielding 0.270 g. of the title product. Combination of the yields of these two recrystallizations gave 0.479 g. of the desired pure product, ethyl 2-[(5-amino-1,2,4-oxadiazol)-3-yl]-2-Z-methoximinoacetate: n.m.r. (CDCl$_3$) δ1.15 (t, 3, C$\underline{H}_3$—CH$_2$—O—), 3.95 (s, 3, C$\underline{H}_3$O—N) 4.25 (q, 2, CH$_3$—C$\underline{H}_2$—O), 8.05 (br s, 2, NH$_2$); i.r. (mull) in cm.$^{-1}$, 3420 (NH), 1730 (CO$_2$Et), 1670; u.v. (methanol) λ=227 nm, ε=11,335.

Step D

Preparation of Sodium 2-[(5-Amino-1,2,4-oxadiazol)-3-yl]-2-Z-methoximinoacetate Ethyl 2-[(5-amino-1,2,4-oxadiazol)-3-yl]-2-Z-methoximinoacetate (4.28 g., 20 mmol) was dissolved in 2B ethanol (50 ml.), followed by addition of 5 N sodium hydroxide solution (4 ml.). This reaction mixture was stirred for 0.75 h. at room temperature, then filtered. The solid collected was washed with 2B ethanol and ether to yield 3.43 g. (82% yield) of cream-colored crystals of sodium 2-[(5-amino-1,2,4-oxadiazol)-3-yl]-2-Z-methoximinoacetate: i.r. (KBr) 1680, 1665, 1615; u.v. (methanol) λ$_{max}$=233, ε=10,391;

Analysis: Calculated for C$_5$H$_5$N$_4$O$_4$Na: C, 28.86; H, 2.42; N, 26.92; Found: C, 27.37; H, 2.91; N, 23.91.

Step E

Preparation of 2-[(5-Amino-1,2,4-oxadiazol)-3-yl]-2-Z-methoximinoacetic Acid Sodium 2-[(5-amino-1,2,4-oxadiazol)-3-yl]-2-Z-methoximinoacetate (1.0 g.) was suspended in ethyl acetate and 1 N hydrochloric acid was added dropwise (6 ml.). The layers were separated and the aqueous layer was rewashed with ethyl acetate. The ethyl acetate layers were combined, dried over magnesium sulfate, filtered and the filtrate was evaporated to yield 0.75 g. of 2-[(5-amino-1,2,4-oxadiazol)-3-yl]-2-Z-methoximinoacetic acid NMR (CDCl$_3$): δ4.0 (s, 3, N—OC$\underline{H}_3$), 7.05 (s, 2, NH$_2$), 8.5 (s, 1, CO$_2$H), (DMSO/d$_6$) δ3.75 (s, 3, N—OM$\underline{e}$), 8.12 (s, 2, NH$_2$).

PREPARATION 2

Preparation of benzhydryl 7β-[2-[(5-amino-1,2,4-oxadiazol)-3-yl]-2-Z-methoximinoacetamido]-3-acetoxymethyl-3-cephem-4-carboxylate 2-[(5-Amino-1,2,4-oxadiazol)-3-yl]-2-Z-methoximinoacetic acid (0.75 g., 4 mmol) was dissolved in a 1:1 v:v tetrahydrofuran/acetonitrile solvent (20 ml.). This solution was stirred as dicyclohexylcarbodiimide (0.5 g., 2.4 mmol), dissolved in the same THF/acetonitrile solvent as above (10 ml.), and was added dropwise. The resultant mixture was stirred for 0.5 h., during which time the dicyclohexylurea precipitated. Benzhydryl 7β-amino-3-acetoxymethyl-3-cephem-4-carboxylate (0.876 g., 2.0 mmol) was added to the solution and stirring was continued for 56 hours. The dicyclohexylurea was collected by filtration and the filtrate was evaporated, triturated with ether and decanted (2X). The ether-insoluble material was dissolved in ethyl acetate, washed with 1 N hydrochloric acid (2X), aqueous sodium bicarbonate solution (2X), and saturated sodium chloride solution (2X). This solution was then dried over magnesium sulfate, filtered and concentrated in vacuo. The resultant material was again triturated with ether and filtered, yielding 0.640 g. of crude material. This material was purified by dry silica gel column chromatography, collecting 25 ml. fractions. A 1:1 v:v ethyl acetate/cyclohexane solution was used as the eluant for the first 25 fractions, followed by elution with a 3:1 v:v ethyl acetate/cyclohexane solvent. Fractions 33 through 42 were combined, evaporated to dryness, dissolved in chloroform and precipitated from the chloroform by the addition of hexane. The precipitate was collected by filtration, washed with ether then dried in vacuo, yielding 0.420 g. of benzhydryl 7β-[2-[(5-amino-1,2,4-oxadiazol)-3-yl]-2-Z-methoximinoacetamido]-3-acetoxymethyl-3-cephem-4-carboxylate: n.m.r. (CDCl$_3$) δ1.90 (s, 3, 3'-OAc), 3.27, 3.55 (ABq, J=6, 2, C$_2$-methylene proton), 4.68, 4.95 (ABq, J=5, 2, C$_3$-methine proton), 4.96 (d, J=1.5, 1, C-6 proton), 5.95 (dd, (J=1.5, 3), 1, C-7 proton), 6.25, (br s, 2, N$\underline{H}_2$), 6.85 (s, 1, C$\underline{H}$Ph$_2$), 7.20 (s, 10, aromatic protons), 8.72 (d, J=3, 1, 7-amido proton).

PREPARATION 3

Preparation of 7β-[2-(5-amino-1,2,4-oxadiazol)-3-yl-2-Z-methoximinoacetamido]-3-acetoxymethyl-3-cephem-4-carboxylic acid Benzhydryl 7β-[2-(5-amino-1,2,4-oxadiazol)-3-yl-2-Z-methoximinoacetamido]-3-acetoxymethyl-3-cephem-4-carboxylate (0.435 g.) was dissolved in a formic acid solution (12 ml., 97–100%) of triethylsilane (0.3 ml.) and stirred for 3 h. The solution was evaporated to dryness, the residue dissolved in ethyl acetate and extracted with 10% aqueous sodium bicarbonate. The sodium bicarbonate solution was washed with ethyl acetate, then layered with ethyl acetate and the resultant solution was acidified to pH 2 with 1 N hydrochloric acid. The ethyl acetate layer was separated and was washed with saturated sodium chloride solution, dried over magnesium sulfate and filtered. The filtrate was concentrated in vacuo and the residue triturated with ether and filtered to yield 0.215 g. of the product compound 7β-[2-[(5-amino-1,2,4-oxadiazol)-3-yl-2-Z-methoximinoacetamido]-3-acetoxymethyl-3-cephem-4-carboxylic acid: n.m.r. (acetone/d$_6$) δ1.7 (s, 3, OAc), 3.15, 3.42 (ABq,(J=6), 2, C-2 methylene protons), 3.67 (s, 3, N—OC$\underline{H}_3$), 4.57, 4.8 (ABq, (J=5), 2, C-3 methylene proton), 4.87 (d, (J=2), 1, C-6 proton), 5.65 (dd, (J=2,2.5), 1, C-7 protons), 7.05 (br s, 2, —N$\underline{H}_2$), 8.25 (d, J=2.5, 1, 7-amido proton).

PREPARATION 4

2-(2-Aminooxazol-4-yl)-2-Z-methoxyiminoacetic acid

Ethyl γ-bromo-α-methoximinoacetoacetate (100 g., 0397 mmol). and urea (91 g., 1.98 mmol), were dissolved in methylethylketone (3 l.) and zinc oxide (16 g., 0.198 mmol) was added. The suspension was stirred under reflux for 48 hours and was then allowed to cool. The solution was filtered and concentrated in vacuo. The dark residue was dissolved in ethyl acetate and the solution filtered. The filtrate was evaporated in vacuo and the residue was chromatographed over activity III neutral alumina. The column was eluted sequentially with neat cyclohexane (1000 ml.), 1:9 v:v ethyl acetate:-cyclohexane (1000 ml.), 2:8 v:v ethyl acetate:cyclohexane (2000 ml.), 3:7 v:v ethyl acetate:cyclohexane (500 ml.), and finally with 1:1 v:v ethyl acetate:cyclohexane until no more product was eluted. Fifty-five fractions were taken, although fractions 51 through 55 were 500 ml. or greater. The crude product was contained in fractions 51, 52, and 53. The three fractions were evaporated to give a semi-crystalline mass, each of which were triturated with ether and filtered to yield 3 pure crops of crystals of product. These crops of crystals were combined with a second crop of crystals obtained from fraction 52 to yield 8.9 g. of ethyl 2-[2-aminooxazol-4-yl]-2-Z-methoximinoacetate.

A mixture of ethyl 2-[2-aminooxazol-4-yl]-2-Z-methoximinoacetate (2.13 g., 10 mmol), triethylamine (1.53 ml., 11 mmol) and dimethylacetamide (25 ml.) were chilled to 0° C. by means of an ice bath. A chilled solution of chloroacetyl chloride (0.939 ml., 11 mmol.) in 10 ml. of dimethylacetamide was added dropwise to the stirred solution. The reaction mixture was stirred for 0.5 hour at 0° C., and for 19 hours at room temperature. The reaction mixture was poured onto ice and the resultant mixture was extracted with ethyl acetate. The ethyl acetate was washed with water, dried over anhydrous magnesium sulfate, filtered and concentrated in vacuo. After evacuating under high vacuum for 24 hours, the residue was triturated with ether and filtered. The mother liquor was evaporated and the residue was recrystallized from carbon tetrachloride to give 0.456 g. of ethyl 2-[2-(2-chloroacetamido)oxazol-4-yl]-2-Z-methoximinoacetate; melting point 91°–92° C.; n.m.r. (CDCl$_3$) $\delta$1.32 (t, 3, —CH$_3$, J=7.5 Hz), 4.0 (s, 3, OC$\underline{H}_3$), 4.1 (s, 2, Cl—C$\underline{H}_2$—), 4.37 (q, 2, —O—C$\underline{H}_2$—, j=7.5 Hz), 7.25 (s, 1, aromatic proton).

Sodium hydroxide (5 N, 2 equivalents plus a 10% excess, 4.6 ml., 22.86 mmol) was added dropwise to a stirred suspension of ethyl 2-[2-(chloroacetamido)oxazol-4-yl]-2-Z-methoximinoacetate (3.0 g., 10.38 mmol) in water (90 ml.). Dissolution of the ester was complete within about 15 to 20 minutes, and stirring was continued for an additional hour. The mixture was chilled and acidified by the dropwise addition of 1 N hydrochloric acid (6 ml.). The aqueous layer was saturated with sodium chloride and the mixture was extracted with large quantities of ethyl acetate. The ethyl acetate extracts were dried over anhydrous sodium sulfate, filtered, combined and concentrated in vacuo, yielding 0.453 g. of 2-(2-aminooxazol-4-yl)-2-Z-methoximinoacetic acid; melting point 170°–174° C. (decompose); n.m.r. (DMSO/d$_6$) $\delta$3.84 (s, 3, NOC$\underline{H}_3$), 6.77 (br, s, 2, amino), $\delta$7.48 (s, 1, aromatic proton).

PREPARATION 5

Benzhydryl 7$\beta$-[2-(2-aminooxazol-4-yl)-2-Z-methoximinoacetamido]-3-acetoxymethyl-3-cephem-4-carboxylate 2-(2-Aminooxazol-4-yl)-2-Z-methoximinoacetic acid (0.261 g., 1 mmol) was dissolved in a mixture of dimethylacetamide (3 ml.) and methylene chloride (3 ml.). Triethylamine (0.139 ml., 1 mmol) was added to this solution and the resultant mixture was added dropwise to a stirred, chilled solution of iso-butylchlorocarbonate in 25 ml. of methylene chloride. The reaction mixture was stirred for 1 hour, at the end of which time a methylene chloride (5 ml.) solution of benzhydryl 7$\beta$-amino-3-acetoxymethyl-3-cephem-4-carboxylate was added dropwise. Initially, the reaction mixture was stirred at 0° to 10° C. and was addlowed to gradually warm to ambient temperature and stirred overnight.

The reaction mixture was evaporated in vacuo and the residue was taken up in ethyl acetate. The ethyl acetate solution was washed sequentially with 1 N hydrochloric acid, 10% aqueous sodium bicarbonate, and a saturated aqueous sodium chloride solution. Removal of the ethyl acetate solvent in vacuo, after drying the solution over sodium sulfate and filtering, resulted in a yellow foam. This crude product mixture was chromatographed over Activity III Silica Gel (100–200 mesh, Woehlm). Elution was begun with 7:3 v:v ethyl acetate:cyclohexane (fractions 1 through 19), then heat ethyl acetate (fractions 20 through 34), and finally 9:1 v:v ethyl acetate:methanol (fractions 34 through 37). The desired product, benzhydryl 7$\beta$-[2-(2-aminooxazol-4-yl)-2-Z-methoximinoacetamido]-3-acetoxymethyl-3-cephem-4-carboxylate, was contained in fractions 14 through 30, and these fractions were combined to yield 0.100 g. of the desired product: n.m.r. (CDCl$_3$) $\delta$1.98 (s, 3, methyl of 3-acetoxymethyl), 3.3 and 3.56 (ABq, 2, C-2), 4.75 and 5.01 (ABq, 2, C-3'), 5.02 (d, 1, C-6), 5.25 (br, s, 2, amino), 5.95 (q, 1, C-7), 7.9 (s, 1, benzyl methine proton), 7.3 (m, 11, phenyl rings and oxazole ring), 8.42 (d, 1, amido proton).

PREPARATION 6

7$\beta$-[2-(2-Aminooxazol-4-yl)-2-Z-methoximinoacetamido]-3-acetoxymethyl-3-cephem-4-carboxylic acid Benzyl 7$\beta$-[2-(2-aminooxazol-4-yl)-2-Z-methoximinoacetamido]-3-acetoxymethyl-3-cephem-4-carboxylate (approximately 100 mg., 0.16 mmol) was dissolved in a mixture of formic acid (97–100%), 4 ml.) and triethylsilane (0.04 ml., 0.25 mmol). The reaction mixture was stirred at room temperature for 3 hours, was diluted with ethyl acetate, and evaporated to a gum. The gum was treated twice with an ethyl acetate/acetonitrile mixture to give a light brown powder. The powder was further dried by evaporation in vacuo for 1 hour. The brown powder was then dried with ether for 0.5 hour, sonnicated, filtered and air-dried to yield 64 mg. (91%) of 7$\beta$-[2-(2-aminooxazol-4-yl)-2-Z-methoximinoacetamido]-3-acetoxymethyl-3-cephem-4-carboxylic acid. n.m.r. (DMSO/d$_6$) $\delta$2.0 (s, 3, acetoxymethyl methyl), 3.4 (m, 2, C-2), 3.85 (s, 3, =NOC$\underline{H}_3$), 4.85 (q, 2, J=16, C-3'), 5.15 (d, 1, J=6, C-6), 5.8 (q, 1, J=4, C-7), 6.85 (s, 2, amino), 7.5 (s, 1, oxazole ring), 9.6 (d, 1, J=9, amido).

PREPARATION 7

7$\beta$-[2-(2-Aminooxazol-4-yl)-2-Z-methoxyiminoacetamido]-3-acetoxymethyl-3-cephem-4-carboxylic acid A mixture of 1-hydroxybenzotriazole monohydrate (1.02 g., 6.68 mmol) and triethylamine (1.138 ml., 8.16 mmol) in dimethylacetamide (8 ml.) was chilled in an ice-acetone bath and a solution of methanesulfonyl chloride (0.57 ml., 7.3 mmol) in 2 ml. of dimethylacetamide was added dropwise. The solution was stirred at 0° to 10° C. for 1.5 hours. A solution of 2-(2-aminooxazol-4-yl)-2-Z-methoximinoacetic acid (1.235 g., 6.68 mmol) in dimethylacetamide (2.5 ml.) containing triethylamine (1.01 ml.) was then added dropwise to the cold mixture, and the solution was stirred at 0° to 10° C. for an additional 1.5 hours. Water (21 ml.) was then added dropwise and within 10 minutes after the water had been added, the product precipitated, was collected by filtration, washed with cold water, and dried in vacuo to yield 1.277 g. (63%) of the product, 1-(N-oxide)benzotriazol-3-yl 2-[2-aminooxazol-4-yl]-2-Z-methoximinoacetamide.

7β-Amino-3-acetoxymethyl-3-cephem-4-carboxylic acid (0.43 g., 1.58 mmol) was suspended in 25 ml. of a 1:1, v:v, water:acetone solvent cooled in an ice bath and triethylamine (0.2 ml., 1.48 mmol) was added dropwise to the stirred solution. After the solution formed, 1-(N-oxide)benzotriazol-3-yl 2-[2-aminooxazol-4-yl]-2-Z-methoximinoacetamide (0.5 g., 1.66 mmol) was added portionwise. The ph of the solution was maintained at approximately 7.5 by the periodic additions of 45% aqueous potassium phosphate solution. After the addition of the benzotriazole amide was complete, the mixture was slowly allowed to warm to room temperature. After approximately 2 hours, dissolution had occurred and the solution was stirred overnight. The acetone was removed, and the aqueous concentrate was diluted with water, layered with ethyl acetate, and the pH of the solution adjusted to pH 2.5 by the addition of 1 N hydrochloric acid. The ethyl acetate layer was then separated, dried, filtered and evaporated in vacuo. The partially crystalline residue triturated with ether and filtered to yield 0.3 g. of 7β-[2-(2-aminooxazol-4-yl)-2-Z-methoxyiminoacetamido]-3-acetoxymethyl-3-cephem-4-carboxylic acid: n.m.r. (DMSO/$d_6$) δ2.0 (s, 3, OAc), 3.32 and 3.61 (ABq, 2, J=18 Hz, C-2 protons), 4.85 (s, 3, OC$\underline{H}_3$), 4.7 and 5.0 (ABq, 2, J=12 Hz, C-3' protons), 5.08 (d, 1, J=4.5 Hz, C-6 proton), 5.72 (q, 1, J=4.5 and 9 Hz, C-7 proton), 6.6 (br, s, 2, amino), 7.38 (s, 1, oxazole aromatic proton), 9.5 (d, 1, J=9 Hz, 7-amido N-proton); u.v. (methanol) λmax=217 ($\epsilon_m$=19,254), λmax=265 ($\epsilon_m$=10,200).

Analysis Calculated: C, 43.74; H, 3.90; N, 15.94. Observed: C, 44.01; H, 3.97; N, 15.75.

EXAMPLE 1 syn-7-[2-(2-Aminooxazol-4-yl)-2-methoxyiminoacetamido]-3-(quinolinium-1-ylmethyl)-3-cephem-4-carboxylate is prepared with trimethylsilylated syn-7-[2-(2-aminothiazol-4-yl)-2-methoxyiminoacetamido]-3-iodomethyl-3-cephem-4-carboxylic acid and quinoline.

EXAMPLE 2 syn-7-[2-(5-Amino-1,2,4-oxadiazol-3-yl)-2-methoxyiminoacetamido]-3-(quinolinium-1-ylmethyl)-3-cephem-4-carboxylate is prepared with trimethylsilylated syn-7-[2-(2-amino-1,2,4-oxadiazol-3-yl)-2-methoxyiminoacetamido]-3-iodomethyl-3-cephem-4-carboxylic acid and quinoline.

EXAMPLE 3 syn-7-[2-(5-Aminoisoxazol-3-yl)-2-methoxyiminoacetamido]-3-(quinolinium-1-ylmethyl)-3-cephem-4-carboxylate is prepared with trimethylsilylated syn-7-[2-(5-aminoisoxazol-3-yl)-2-methoxyiminoacetamido]-3-iodomethyl-3-cephem-4-carboxylic acid and quinoline.

EXAMPLE 4 syn-7-[2-(2-Aminooxazol-4-yl)-2-methoxyiminoacetamido]-3-(6-hydroxyquinolinium-1-ylmethyl)-3-cephem-4-carboxylate is prepared with 6-hydroxyquinoline and the corresponding silylated 3-iodomethyl cephalosporin.

EXAMPLE 5 syn-7-[2-(5-Amino-1,2,4-oxadiazol-3-yl)-2-methoxyiminoacetamido]-3-(5-aminoquinolinium-1-ylmethyl)-3-cephem-4-carboxylate is prepared with the corresponding 3-iodomethyl silylated cephalosporin and 5-aminoquinoline.

EXAMPLE 6 syn-7-[2-(5-Amino-1,2,4-oxadiazol-3-yl)-2-methoxyiminoacetamido]-3-(4-carbamoylquinolinium-1-ylmethyl)-3-cephem-4-carboxylate is prepared with the corresponding silylated 3-iodomethylcephalosporin and quinoline-4-carboxamide.

EXAMPLE 7 syn-7-[2-(2-Aminooxazol-4-yl)-2-ethoxycarbonylmethoxyiminoacetamido]-3-(3-methylquinolinium-1-ylmethyl-3-cephem-4-carboxylate is prepared with the corresponding silylated 3-iodomethyl cephalosporin and 3-methylquinoline.

EXAMPLE 8 syn-7-[2-(5-Amino-1,2,4-oxadiazol-3-yl)-2-hydroxyiminoacetamido]-3-(5-hydroxyquinolinium-1-ylmethyl)-3-cephem-4-carboxylate is prepared with the corresponding silylated 3-iodomethyl cephalosporin and 5-hydroxyquinoline.

EXAMPLES 9–23

In the following Examples the compounds of the invention (formula 1) are prepared with the corresponding 3-iodomethyl silylated cephalosporin (formula 3) and the indicated quinoline.

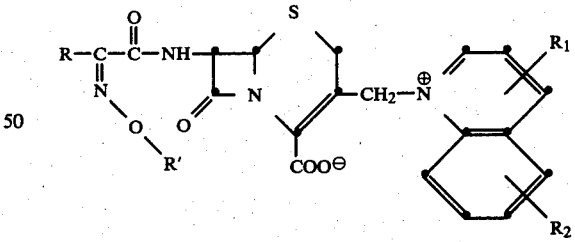

| Example No. | R* | R' | $R_1$ | $R_2$ |
|---|---|---|---|---|
| 9 | 2AO | CH$_3$ | 3-Cl | H |
| 10 | " | CH$_2$—COOC$_2$H$_5$ | H | H |
| 11 | " | —C(CH$_3$)$_2$COOH | 4-OH | 6-Cl |
| 12 | 5AOD | CH$_3$ | H | 8-OH |
| 13 | " | CH$_3$ | H | 8-CH$_3$O |
| 14 | " | " | 4-CF$_3$ | H |
| 15 | " | —CH$_2$COOCH$_3$ | 3-CH$_3$ | 5-OH |
| 16 | " | CH$_3$ | 4-CONH$_2$ | H |
| 17 | " | CH$_3$ | 4-Br | 6-CONH$_2$ |
| 18 | " | —C(CH$_3$)$_2$COOH | 4-CONH$_2$ | H |
| 19 | " | " | COOH | H |

-continued

| Example No. | R* | R' | $R_1$ | $R_2$ |
| --- | --- | --- | --- | --- |
| 20 | 5AIO | $CH_3$ | 4-$CONH_2$ | H |
| 21 | " | " | 4-OH | H |
| 22 | " | " | 4-Cl | 6-Cl |
| 23 | " | —$CH(CH_3)COOH$ | H | 5-$NH_2$ |

*2AO is 2-aminooxazol-4-yl; 5AOD is 5-amino-1,2,4-oxadiazol-3-yl; 5AIO is 5-aminoisoxazol-3-yl.

We claim:

1. A compound of the formula

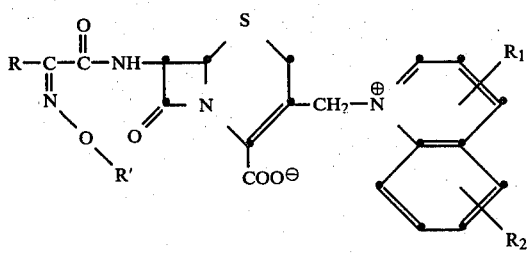

wherein R is an amino-substituted heterocyclic of the formulas

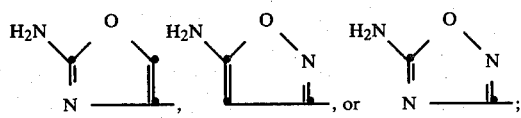

R' is hydrogen, $C_1$–$C_4$ alkyl, a carboxy-substituted alkyl or carboxy-substituted cycloalkyl group of the formula

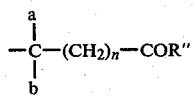

wherein a and b when taken separately are independently hydrogen or $C_1$–$C_3$ alkyl, and when taken together with the carbon atom to which they are attached form a $C_3$–$C_7$ carbocyclic ring; R" is hydroxy, amino, $C_1$–$C_4$ alkoxy, and when R" is hydroxy carboxy-protected esters thereof; or R' is an N-substituted carbamoyl group of the formula

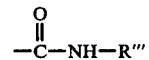

wherein R'" is $C_1$–$C_3$ alkyl, phenyl, or $C_1$–$C_3$ alkyl substituted by phenyl; $R_1$ and $R_2$ independently are hydrogen, amino, $C_1$–$C_4$ alkylamino, di-($C_1$–$C_4$) alkylamino, hydroxy, $C_1$–$C_4$ alkoxy, halogen, $C_1$–$C_4$ alkyl, cyano, trifluoromethyl, sulfo(—$SO_3H$), aminosulfonyl (—$SO_2NH_2$), carboxy, $C_1$–$C_4$ alkoxycarbonyl, carbamoyl, thiocarbamoyl, hydroxy-substituted $C_1$–$C_3$ alkyl, formyl, or $C_2$–$C_4$ alkanoyl; and the pharmaceutically acceptable non-toxic salts thereof.

2. The compound of claim 1 wherein $R_1$ and $R_2$ are hydrogen.

3. The compound of claim 2 wherein R' is $C_1$–$C_4$ alkyl.

4. The compound of claim 3 wherein R' is methyl.

5. The compound of claim 4 wherein R is 2-aminooxazol-4-yl or 5-amino-1,2,4-oxadiazol-3-yl.

6. The compound of claim 1 wherein $R_1$ or $R_2$ is an amino group.

7. The compound of claim 6 wherein R' is methyl.

8. The compound of claim 1 wherein $R_1$ or $R_2$ is a hydroxy group.

9. The compound of claim 8 wherein R' is methyl.

10. A pharmaceutical formulation suitable for the treatment of infectious disease which comprises a therapeutically effective amount of an antibiotic compound of claim 1 and a pharmaceutically acceptable diluent.

11. The formulation of claim 10 where in said antibiotic compound $R_1$ and $R_2$ are hydrogen.

12. A method for treating bacterial infections in a mammal which comprises administering in a dose between about 100 mg. and about 2 g. of an antibiotic compound of claim 1 or a pharmaceutically acceptable salt thereof.

13. The method of claim 12 where in said antibiotic compound $R_1$ and $R_2$ are hydrogen.

* * * * *